(12) United States Patent
Fredriksson

(10) Patent No.: US 11,413,474 B2
(45) Date of Patent: Aug. 16, 2022

(54) SYSTEM AND METHOD FOR MODELLING OF DOSE CALCULATION IN RADIOTHERAPY TREATMENT PLANNING

(71) Applicant: RaySearch Laboratories AB, Stockholm (SE)

(72) Inventor: Albin Fredriksson, Stockholm (SE)

(73) Assignee: RaySearch Laboratories AB, Stockholm (SE)

( * ) Notice: Subject to any disclaimer, the term of this patent is extended or adjusted under 35 U.S.C. 154(b) by 134 days.

(21) Appl. No.: 16/500,419

(22) PCT Filed: Apr. 3, 2018

(86) PCT No.: PCT/EP2018/058413
§ 371 (c)(1),
(2) Date: Oct. 3, 2019

(87) PCT Pub. No.: WO2018/185063
PCT Pub. Date: Oct. 11, 2018

(65) Prior Publication Data
US 2020/0121953 A1    Apr. 23, 2020

(30) Foreign Application Priority Data
Apr. 5, 2017 (EP) .................................... 17164934

(51) Int. Cl.
*A61N 5/10* (2006.01)
*G16H 20/40* (2018.01)

(52) U.S. Cl.
CPC .......... *A61N 5/103* (2013.01); *A61N 5/1031* (2013.01); *A61N 5/1043* (2013.01); *G16H 20/40* (2018.01); *A61N 2005/1087* (2013.01)

(58) Field of Classification Search
CPC .... A61N 5/103; A61N 5/1031; A61N 5/1042; A61N 5/1043; A61N 2005/1087
See application file for complete search history.

(56) References Cited

U.S. PATENT DOCUMENTS

| | | | |
|---|---|---|---|
| 2013/0303825 A1 | 11/2013 | Bert et al. | |
| 2014/0005464 A1* | 1/2014 | Bharat | ................ G10L 21/0208 600/1 |

(Continued)

OTHER PUBLICATIONS

Bock et al., Towards Robust Adaptive Radiation Therapy Strategies, Nov. 4, 2016, Medical Physics (Year: 2016).*

(Continued)

*Primary Examiner* — Eliza W Osenbaugh-Stewart
(74) *Attorney, Agent, or Firm* — Faegre Drinker Biddle & Reath LLP

(57) ABSTRACT

A method is proposed for evaluating the robustness of a radiotherapy treatment plan. The method comprises, defining a number of scenarios, each comprising one or more errors for each fraction of the plan, including interfractional and/or intrafractional errors, and calculating a dose distribution resulting from the scenario;
The robustness of the plan is then evaluated based at least one of the following
  i. the probability of fulfilling a set of clinical goals estimated as the clinical goal fulfilment over the scenarios
  ii. the range of DVH values over the scenarios
  iii. dose statistics for dose distributions defined as voxel-wise aggregates over the scenario doses.

18 Claims, 4 Drawing Sheets

(56) References Cited

U.S. PATENT DOCUMENTS

2016/0059039 A1 3/2016 Liu
2017/0014642 A1 1/2017 An et al.

OTHER PUBLICATIONS

Beckham, W. A., et al., "A fluence-convolution method to calculate radiation therapy dose distributions that incorporate random set-up error," Physics in Medicine and Biology 47 (2002) pp. 3465-3473.
Fredriksson, Albin, et al., "Maximizing the probability of satisfying the clinical goals in radiation therapy treatment planning under setup uncertainty," Medical Physics, vol. 42, No. 7, 2015, pp. 3992-3999.
Lowe et al., "Incorporating the effect of fractionation in the evaluation of proton plan robustness to setup errors," Physics in Medicine & Biology, vol. 61, pp. 413-429, 2016.
Perkó et al., "Fast and accurate sensitivity analysis of IMPT treatment plans using Polynomial Chaos Expansion," Physics in Medicine & Biology, vol. 61, pp. 4646-4664, 2016.

\* cited by examiner

SYSTEM AND METHOD FOR MODELLING OF DOSE CALCULATION IN RADIOTHERAPY TREATMENT PLANNING

This application is the National Stage of International Application No. PCT/EP2018/058413, filed Apr. 3, 2018, and claims benefit of European Patent Application No. 17164934.6, filed Apr. 5, 2017, the entire contents of which are incorporated by reference herein.

TECHNICAL FIELD

The present invention relates to a system and a method for evaluating the robustness of a radiotherapy treatment plan.

BACKGROUND

In radiotherapy, ionizing radiation is used to kill or control malignant cells in a patient's body. It is important that the radiation is delivered in such a way that the radiation to the malignant tissue, and to the surrounding tissue that should be protected, does not deviate too much from the clinical goals set.

Misalignment of a patient relative to the beam can lead to large differences between the planned and the delivered dose distributions in external beam radiation therapy. The conventional approach to take such errors into account is to apply margins around any region of interest during treatment planning to ensure that a target receives the required dose, or a healthy organ receives a sufficiently low dose, even if it the patient is shifted relative to the beam. As an alternative, robust optimization may be used, in which a number of different possible scenarios are defined and the treatment plan is optimized to yield satisfactory results for all possible scenarios.

Radiation therapy is often delivered to a patient in a number of fractions, typically up to 30 or 40. The radiation delivered in each fraction can be the same as in other fractions, or the radiation can be different between the fractions. In addition to a systematic error (e.g. setup errors during image acquisition, image artifacts, errors in the conversion from CT densities to stopping power, etc.) caused in the planning, which will affect every fraction in the same way. There may also be random errors for each fraction, and even within fractions. This includes setup errors when the patient is positioned for treatment, organ motion, geometry changes due to weight loss, and so on. This means that when considering the whole treatment there will typically be a large number of possible scenarios resulting from combinations of different errors over the fractions.

It is often advantageous to evaluate the robustness of a radiotherapy treatment plan, to assess how much the result will be affected for different possible scenarios. This is generally achieved by time-consuming exact scenario dose calculations. Alternatively, the need to reduce computational effort will lead to inexact approximations.

Perko et al. 2016, Fast and accurate sensitivity analysis of IMPT treatment plans using Polynomial Chaos Expansion, Physics in Medicine and Biology, 21 Jun. 2016, create a model of the dose engine based on a number of scenario dose calculations. This model is used to compute approximate scenario doses. Such a method still requires a relatively large number of exact scenario dose calculations, for example 217, to create the model of the dose engine. Moreover, it has no mechanism for taking errors between fractions or errors within fractions into account.

Lowe et al. 2015, Incorporating the effect of fractionation in the evaluation of proton plan robustness to setup errors, Physics in Medicine and Biology 16 Dec. 2015, have proposed to base the robustness assessment on very few exact scenario dose calculations, for example 14, and to take the voxel-wise worst case scenario dose as an indication of the robustness. There are typically a much higher number of possible scenarios, and limiting the number of scenario doses, as proposed by Lowe et al., will normally not give a precise representation of the doses that a given voxel will receive. Nevertheless, 14 exact scenario dose calculations is still a larger number than desired, and the method does not take errors within fractions into account. Because of the limited number of scenarios, the method cannot be used to accurately calculate the probability of fulfilling the clinical goals.

Beckham et al. 2002, A fluence-convolution method to calculate radiation therapy dose distributions that incorporate random set-up error, Physics in Medicine and Biology, 7 Oct. 2002 approximate the effects of random setup errors for photon therapy. They do so by convolving the fluence by a Gaussian kernel to generate a single dose distribution that approximates the effect of random setup errors. However, such a single dose distribution is only accurate if the number of fractions is very large and is thus of limited usefulness for hypofractionated treatments. Moreover, it does not take systematic errors or errors within fractions into account, and cannot be used to calculate statistics for clinical goal fulfillment or DVH ranges or envelopes.

There is a desire to find a way to evaluate the robustness of a radiotherapy treatment plan that overcomes the above drawbacks.

SUMMARY OF THE INVENTION

It is an object of the present invention to propose a way to evaluate the robustness of a radiotherapy treatment plan that will present a more exact result than former methods while at the same time being computation efficient.

The invention proposes a method for evaluating the robustness of a radiotherapy treatment plan, comprising a number of treatment fractions, comprising the steps of a. Obtaining a plan to be evaluated;
b. Defining a scenario comprising one or more errors for each fraction;
c. Calculating a dose distribution resulting from the scenario, wherein the contribution from each beam to the total dose distribution resulting from a scenario is approximated by a single beam dose calculation;
d. Repeating steps b. and c. for a number of different scenarios;
e. Evaluating the robustness of the plan based on at least one of the following:
  i. the probability of fulfilling a set of clinical goals estimated as the clinical goal fulfillment over the scenarios,
  ii. the range of DVH values over the scenarios,
  iii. dose statistics for dose distributions defined as voxel-wise aggregates over the scenario doses.

The method according to the invention enables the resulting dose distributions for a number of different scenarios to be calculated faster and more accurately than with the prior art methods. Errors caused in any part of the treatment can be taken into account for evaluating the possible outcomes of the plan, including systematic errors, interfractional errors and intrafractional errors, to produce a reliable evaluation with a manageable computational effort. A scenario is a description of one possible series of errors over the treatment, and can describe systematic errors, interfractional errors that occur between the treatment fractions, or intrafractional errors that occur within the treatment fractions, or combinations thereof.

Moreover, the method according to the invention retains the correlation between voxels and can therefore be used to calculate statistics for the clinical goals.

According to a preferred embodiment, the steps a-d are performed at least once for each of the elements in at least one of the following:
  One or more patient images
  One or more artificial patient images
  One or more density errors
This enables the evaluation of the plan based on real or artificial patient images, and/or density errors. Artificial patient images may be created to resemble predicted changes in the patient over time. Such changes may be caused by, for example, movements or weight loss.

Typically, the one or more errors for each fraction includes at least a systematic error that affects all fractions and/or at least a fraction-specific error.

The contribution from each beam to the total dose distribution resulting under a scenario is preferably approximated by a single beam dose calculation. The actual implementation of this differs with the type of treatment. When used for fluence-based treatments, this involves using a single fluence distribution for each beam direction and energy to calculate an approximation of the total dose distribution resulting from the plan when under a scenario. This single fluence distribution for each beam and energy may for example be calculated as the sum of the fluence distributions for all fractions translated according to their corresponding setup errors projected onto the fluence plane of the beam.

When the inventive method is used for a spot scanning ion based treatment plan, this means that a single set of spot weights for each beam is used to calculate an approximation of the total dose distribution resulting from the plan under a scenario.

This may involve calculating the single set of spot weights for each beam as the sum of the spot weights for each fraction, as follows: translating the spot positions according to the setup error of the fraction according to the scenario, projected onto the spot plane, changing the energy of the spots according to the range or density error, and allocating the spot weights associated with the translated spot positions to the planned (non-translated) spot positions by interpolating spot weights between spots.

In one embodiment, the fluence distribution in each fraction is scaled according to the constituent of its corresponding setup error that is orthogonal to the fluence plane of the beam.

Preferred embodiments further comprise the step of obtaining a set of clinical goals, including at least one clinical goal for the plan to be evaluated. The set of clinical goals on which the evaluation is based is preferably the set of clinical goals used to create the plan to be evaluated. Suitably the method then comprises the further step of determining the probability of fulfilling at least one clinical goal and using this probability in the evaluation.

The step of interpolating spot weights between spots preferably comprises the steps of determining auxiliary spots at a distance from the planning spots, said distance depending on at least one assumed shift in the relative position between the patient and the spot planes or the radiation source, and including the auxiliary spots in the interpolation. In the interpolation, the weights of the translated spots are thus typically assigned to the planned spots as well as to the auxiliary spots. The planned spots and the auxiliary spots are then used in the subsequent dose calculation.

For radiation therapy, there is a known linear correlation between the fluence and the dose. According to the invention, this correlation is used to calculate the accumulated dose based on an approximate accumulated fluence over the exact number of fractions, rather than calculating the dose for either a single fraction or an infinite number of fractions, as is done according to the prior art methods.

The invention also relates to a computer program product comprising computer readable code means which, when run in a computer will cause the computer to perform a method according to the above. This may include a memory device, such as a non-transitory memory comprising the code means.

The invention also relates to a treatment planning system comprising a processor, a data memory comprising data for obtaining a treatment plan, including a set of clinical goals to be used for planning, and a program memory comprising a computer program product according to the above.

BRIEF DESCRIPTION OF THE DRAWINGS

The invention will be described in more detail in the following, by way of example and with reference to the appended drawings, in which.

BRIEF DESCRIPTION OF THE DRAWINGS

In general, according to preferred embodiments of the invention a large number of total doses for simulated treatments are computed, where the total dose is the sum of the doses over the treatment fractions.

Figure 1:
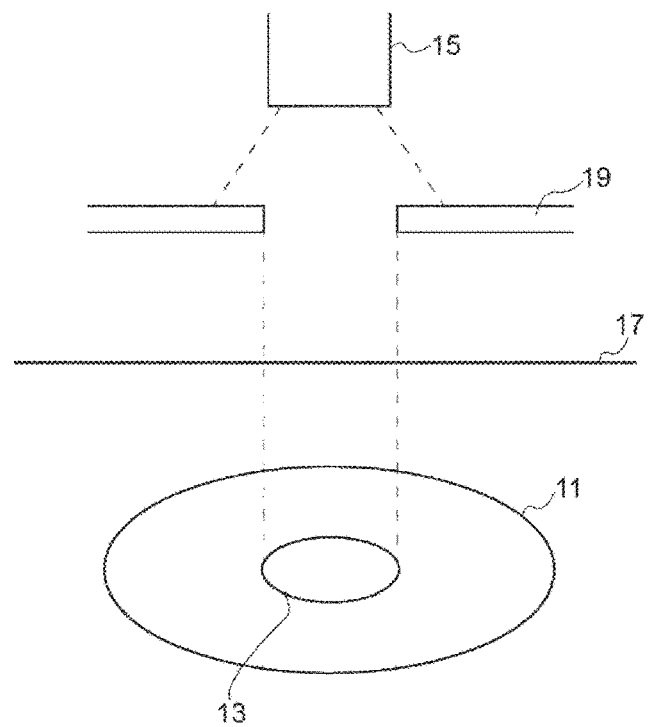
FIG. 1 illustrates a first schematic cross-section of a patient undergoing radiotherapy treatment.

FIG. 1 illustrates schematically a treatment setup, including a schematic cross-section 11 of a patient having a tumour 13. A radiation source 15 is placed above the patient. Between the radiation source 15 and the patient a fluence plane 17 is defined, in which the fluence resulting from the radiation is calculated. Between the radiation source 15 and the fluence plane, there is a collimator 19 or similar element limiting the cross-section of the beam. Typically, in photon therapy, the open area of the collimator can be varied between fractions, and also within a fraction, to determine how much radiation should reach a particular portion of the patient. As will be understood, the Figure is a two-dimensional representation of a three-dimensional situation.

If the patient 11 is shifted relative to the radiation source 15, and to the fluence plane, the dose to the patient will be deformed compared to the intended dose. Normally, there is a shift of the patient in the planning phase, which will affect all treatment fractions in the same way, and a random shift of the patient in each fraction. It is impossible to predict the direction and magnitude of these shifts.

Figure 2:
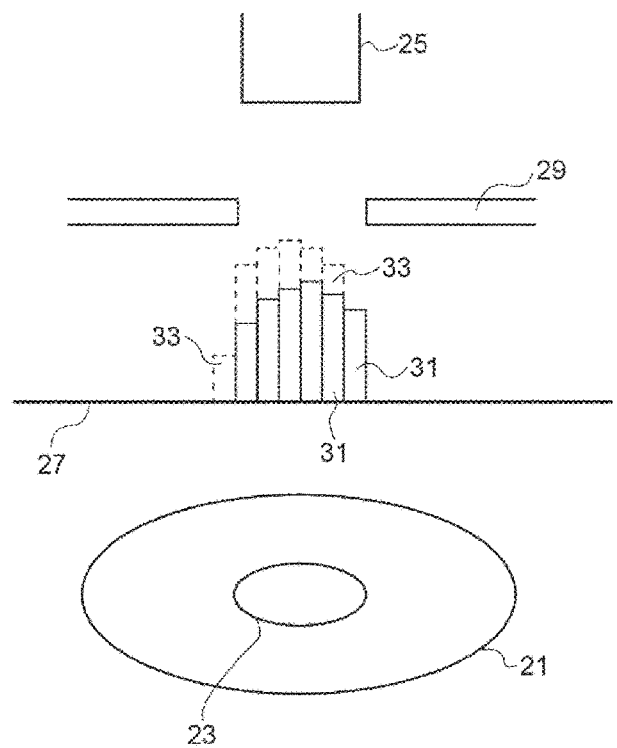
FIG. 2 illustrates a second schematic cross-section of a patient undergoing radiotherapy treatment.

FIG. 2 illustrates the function of the method for a photon based radiotherapy treatment plan. As in FIG. 1, a patient 21 having a tumour 23 is shown. A radiation source 25 is placed above the patient and a fluence plane 27 is defined between the radiation source 25 and the patient. Between the radiation source 25 and the fluence plane, there is a collimator 29 or similar element limiting the cross-section of the beam.

The fluence will vary over the irradiated area, as is indicated by solid boxes 31 of different heights shown in the fluence plane, corresponding to a first fraction. Although FIG. 2 shows each component of the fluence in only one dimension, the fluence will be distributed in two-dimensional sub-areas parallel to the fluence plane. These sub-areas are referred to as bixels (beam pixels) and each bixel will receive an amount of radiation determined by the open time of the corresponding area of the collimator, along with radiation due to such factors as leakage and feathering. The 2D map of fluence over the fluence plane is called a fluence distribution. The fluence of a second fraction is indicated by dashed boxes 33 shifted to the left added onto the boxes of the first fraction. For a normal radiotherapy treatment, a number of such fractions, for example 20 or more, will be delivered to the patient over a period of several weeks.

The radiation of each fraction results in a fraction dose to the patient, which will vary over the irradiated volume. The total radiation of all fractions results in an accumulated dose to the patient. When there are no errors, that is, if the patient's geometry is static over the full treatment, the accumulated dose to the patient has a linear relationship with the fluence accumulated in the fluence plane over all fractions. This means that the accumulated fluence from a bixel can be calculated by adding the open time of the corresponding area of the collimator for all fractions, and similarly, the accumulated fluence distribution over the patient can be calculated by adding the fluence distributions for all fractions. Then the accumulated fluence distribution can be used to calculate the accumulated dose.

In reality, the patient is not in the exact same position during delivery as during planning, as illustrated by the solid and dashed boxes, each representing a fraction fluence. The patient also typically moves during each fraction. Thus, the patient will move relative to the radiation source, and hence also the fluence plane, so a given bixel will affect the patient differently under different fractions or even within a given fraction. This means that the accumulated fluence from a given bixel cannot be used directly to calculate the accumulated dose to the patient.

To simplify the calculations and enable an accumulated fluence from a given bixel to be used to calculate the accumulated dose to the patient, the invention utilizes an approximation where the patient is considered to be fixed relative to the radiation source and the fluence plane. The relative movement of the patient to the radiation source is approximated as a shift, and possibly interpolation and scaling, of the fluence distribution in the fixed fluence plane. The shift in the fluence plane is determined as the projection of the shift of the patient onto the fluence plane. The effect of the approximation is that when the fluence distribution is shifted, the fluence that was previously delivered through bixel x is now approximated as delivered through bixel y, which has a position relative to the source that is different from that of bixel x, and the radiation of which thus has a different direction and divergence than that of bixel x. In reality, the divergence of the radiation is not changed as a result of the patient moving. If a scaling is performed, it can be calculated by the inverse square law from the component of the shift of the patient that is orthogonal to the fluence plane. For example, if the patient is shifted away from the source under one fraction, the fluence component of that fraction is thus scaled down in accordance with the shift and the inverse square law. Using the approximation described above, the accumulated fluence distribution including an error for each fraction, or even multiple errors within each fraction, can be calculated as the sum of the fluence distributions shifted and scaled in accordance with the errors. The accumulated fluence distributions can then be used to calculate the accumulated dose to the patient.

The method according to the invention is based on the assumption that there is a systematic setup and/or density error, which is made during planning, and which will affect every fraction in the same way. In addition, there is a fraction-specific interfractional error, which will be treated as a random error per fraction, and possibly one or more fraction-specific intrafractional errors, which will be treated as a number of random errors within each fraction. To determine the robustness of a plan, different possible sets of errors affecting the dose delivery will be defined and the resulting dose for each such set will be determined and compared to the clinical goals of the plan. A set of errors will comprise one systematic error which is the same for all fractions, one interfractional random error per fraction, which will vary between fractions, and zero or more intrafractional random errors per fraction, which will vary within each fraction.

Each error reflects a deviation in the patient's physical geometry relative to the planning image. For each given beam, the error will be defined in two geometrical dimensions, possibly in combination with a scale factor. For calculating the total dose, however, the sum of doses resulting from several beams has to be calculated. The physical position and/or geometry of the patient may vary in three dimensions, or four dimensions if the range is also to be taken into account. A three-dimensional setup error will be projected to fluence displacements in two dimensions and possibly also a scale factor, which will typically be unique to each beam. A range error due to a difference in the patient's density will also affect the beams differently.

Figure 3:
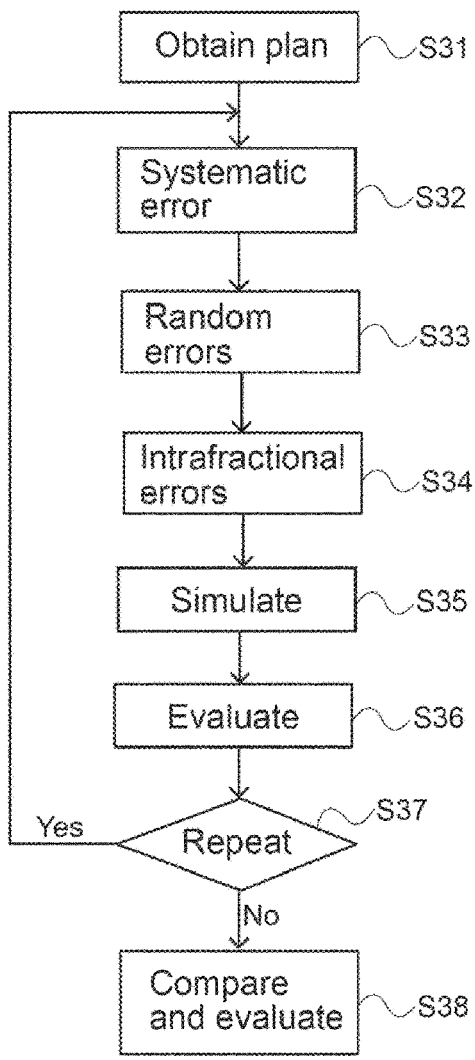
FIG. 3 is a flow chart of a first embodiment of the inventive method.

FIG. 3 is a flow chart of the method according to the invention. In step S31, a treatment plan that is to be evaluated is obtained. The plan may be obtained in any suitable way. Typically, a plan that has already been calculated is selected for evaluation. The manner in which the plan was calculated is not important. A set of input data that may be used to evaluate the plan is also typically obtained at this stage, although it may be obtained at any point during the procedure as long as they are available for the comparing and evaluation step S38. This set of input data may comprise a set of clinical goals comprising one or more goals, typically the clinical goals used as input when optimizing the plan. Alternatively, the input data may be based on DVH data from simulated treatments. A third option is to use voxel-wise dose statistic, presented in the ordinary way of presenting a normal dose distribution in a two-dimensional or three-dimensional image of the patient. In steps S32 and S33 a scenario is defined in terms of deviations from the setup that was assumed when planning.

In step S32 a systematic error affecting all fractions is determined. The systematic error may be a result of, for example, the patient not being perfectly aligned when the planning scans are obtained. Of course, the systematic error may be set to zero, but it is likely that in each case there will be some misalignment between the plan and the actual situation.

In step S33 an interfractional random error is selected for each of the treatment fractions of the plan. Again, one or more errors may be set to zero.

In step S34 zero or more intrafractional random errors are selected for each of the treatment fractions of the plan. Again, one or more errors may be set to zero.

In step S35 a simulation is performed to determine the dose distribution from the current scenario. For a photon based treatment plan, or plans of other modalities using bixel grids to represent the fluence, this can be achieved for each sub-area such as a bixel by determining how the accumulated time the bixel is open over the accumulated duration of all fractions. To do this, the approximation is utilized that the fluence is translated, and possibly interpolated and scaled, in the fixed fluence plane as an effect of the errors. Based on this accumulated open time the accumulated delivered dose to each sub-volume of the patient can be calculated.

Step S36 is an optional step, in which the clinical goals are evaluated on the dose of the current simulated treatment. By counting the number of simulated treatments under which a clinical goal is fulfilled, the probability of fulfilling the clinical goal can be estimated, and there is no requirement to store the doses of all scenarios in memory simultaneously. The evaluation may be based on weighted contributions of each of the simulated treatments, depending on the probability of the likelihood of the corresponding scenario.

After simulation and evaluation, there is a decision step S37, whether more scenarios should be simulated. If yes, go to step S32, if no, go to step S38. As will be understood, the loop in this flow chart is only for illustrative purposes, to discuss each of the steps and should not be taken to mean that only one simulation can be carried out at any given time. As the skilled person will understand, it is possible to perform several simulations in parallel.

The loop from step S32 to S37 is repeated as many times as deemed necessary, depending on the number of scenarios to be considered. Typically, several hundred, or even several thousand scenarios are considered.

In step S38, the resulting dose distributions calculated in step S34 are evaluated. Evaluation can be performed in several ways, and may be selected automatically or by means of user input. For example, clinical goals can be evaluated. Preferably, the probabilities of the clinical goals being fulfilled, either independently or conditionally or both, is calculated. A way of calculating these probabilities will be discussed below. The calculated probabilities are used to evaluate the robustness of the plan. Alternatively, DVHs for all scenarios or DVH bands based on the range of variation of the DVHs over the scenarios can be presented. Another alternative is to exhibit voxel-wise statistics such as voxel-wise minimum or maximum or quantile doses over the scenarios. Alternatively, the comparison may be performed for each scenario as a part of step S36 and only the final evaluation performed in step S38.

In spot scanning proton therapy, the protons are focused into small sub-beams called spots, which are steered to precise positions within the patient. A spot is defined by the direction of the beam and its energy. The spot weight of a particular spot is determined by the time the beam irradiates in that particular direction and with that particular energy.

Figure 4:
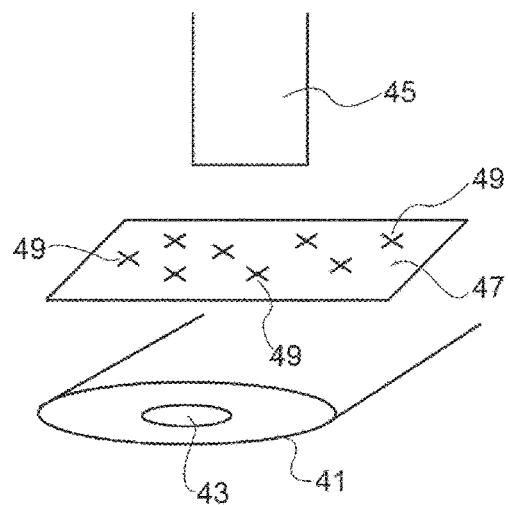
FIG. 4 illustrates a third schematic cross-section of a patient undergoing radiotherapy treatment.

FIG. 4 illustrates spot scanning proton therapy. As in FIG. 1, there is a patient 41 having a tumour 43. A radiation source 45 is placed above the patient. Between the radiation source 45 and the patient a spot plane 47 is defined for each energy of the beam. The spot plane and the patient are schematically shown in three dimensions, to indicate the positions of spots in the spot plane, i.e., the point within the spot plane which the spot traverses. A number of spots 49 are shown in the spot plane.

For spot scanning methods, the invention approximates a movement of the patient relative to the source and the spot planes as a shift of the positions of the spots in the spot plane from intended to actual positions. This means that the invention considers the patient, the source and the spot plane to be fixed relative to each other, similar to how it considers the patient, the source, and the fluence plane to be fixed relative to each other for fluence based treatments. The shift of the positions of the spots in a spot plane is determined as the projection of the shift of the patient onto the spot plane. Shifting the positions of the spots makes dose calculations difficult for several reasons. First, the spots are usually distributed arbitrarily and not on a regular grid. Moreover, even when the spots are distributed regularly, setup errors usually do not match the spot spacing. Also, the spot weights must be translated in three dimensions, to take range uncertainty into account as well as position. This means that the shift of each Bragg peak resulting from the density being other than planned is calculated and approximated as a change in energy, and the positions of the spot in the spot planes of different energy layers usually do not line up.

To account for the effects of the relative movement between the patient and the positions of the spots in the spot planes, the invention uses the translated positions of the spots as input to an interpolation, and allocates the spot weights associated with the translated spot positions to the existing (non-translated) spot positions according to the interpolation. Such interpolation introduces errors, which will increase with increasing spot distance. Hence, the accuracy will be lower if the spots are far apart.

According to embodiments of the invention, for each fraction of each treatment to be simulated, the positions of the spots shifted according to the setup and range error are calculated. Using the set of all possible spot positions, auxiliary spots are selected. Auxiliary spots are preferably selected in a way that keeps the total number of spots as well as the interpolation error small. This can be achieved in different ways known in the art, for example, by clustering or various types of grids. Alternatively, spots can be precalculated on a sufficiently fine and large grid to allow interpolation with desired accuracy without requiring to calculate the shifted spot positions according to each fraction of each treatment to be simulated beforehand.

Figure 5:
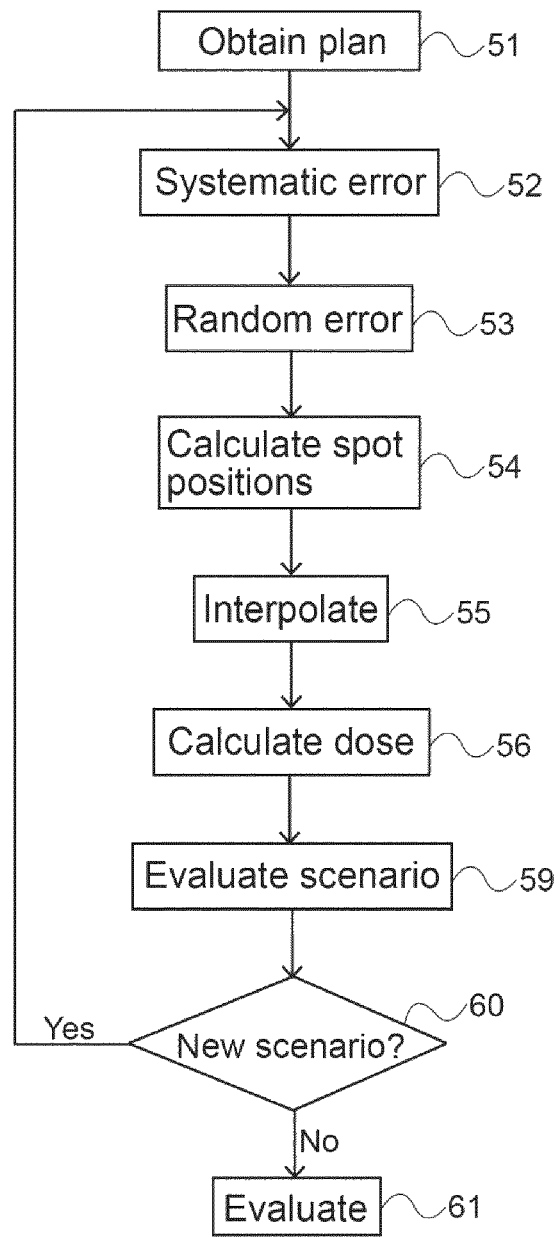
FIG. 5 is a flow chart of a second embodiment of the inventive method.

FIG. 5 is a flow chart illustrating how the inventive method can be applied to spot scanning treatment plans.

In a first step S51 a spot scanning proton treatment plan is obtained including a number of spots which will be referred to here as planning spots. As in step S31 it is not important how the plan was calculated. A set of input data for evaluating the plan is also preferably obtained at this stage, although as for the procedure of FIG. 3, it may be obtained at any point during the procedure as long as they are available for the comparing and evaluation step S61. This may, for example be a set of clinical goals comprising one or more goals, typically the clinical goals used as input when optimizing the plan.

In step S52 a systematic error for a scenario is determined, which will affect all treatment fractions in the same way. In step S53 a random error for each fraction in this scenario is determined. This may optionally include selecting one or more intrafractional random errors for each of the treatment fractions of the plan. Again, one or more errors may be set to zero.

In step S54, shifted planning spot positions for all fractions, or even for each error within each fraction, are determined as shifts of the planning spot positions according to the setup errors projected onto the spot plane. In doing so, the spot weight may also be scaled, for example, according to the inverse square law and the component of the setup error that is orthogonal to the spot plane, and changes of energy according to the range error.

Preferably auxiliary spots have been precalculated by calculating shifted planning spot positions for all fractions, or even all errors within each fraction, in all treatments to be simulated and using these shifted planning spot positions to determine the positions of auxiliary spots. The set of planning spots and auxiliary spots is referred to as the set of interpolation spots. Alternatively, a grid of auxiliary spots encompassing all possible errors to be considered can be precalculated, thus dispensing the need to determine which simulated treatments to consider beforehand.

Next, in step S55 an interpolation is performed to determine the weight contribution in each of the interpolation spots based on the weight in the shifted planning spot positions adjacent the position of the interpolation spot in question. The weights of the displaced planning spots are distributed to and accumulated for the interpolation spots by interpolation (such as nearest neighbour interpolation or scattered data interpolation for arbitrary grids, or bi- or trilinear interpolation for regular grids).

Step S54 and S55 could be performed either sequentially, such that the shifted planning spot positions of all errors within all fractions are first calculated and the interpolation for all of them is subsequently performed, or intermixed, such that for each error within each fraction, the shifted planning spot positions are determined and the interpolation is performed.

Finally, in step S56, the accumulated weight of each interpolation spot is used to calculate the dose contribution from this spot, and the dose distribution for the simulated treatment is calculated as the sum of the dose contributions of all interpolation spots.

Step S59 is an optional step, in which the clinical goals are evaluated on the dose of the current simulated treatment. By counting the number of simulated treatments under which a clinical goal is fulfilled, the probability of fulfilling the clinical goal can be estimated, and there is no requirement to store the doses of all scenarios in memory simultaneously. In step S60, it is determined if another scenario should be considered. If yes, the process returns to step S52, and the loop S52-S60 described above is performed again for another scenario. The loop may be repeated for as many scenarios as are deemed necessary. The decision in step S60 may be based on different criteria. Normally, a predetermined number of scenarios will be considered before continuing to step S61. In step S61, the probability of fulfilling each of the clinical goals is evaluated. It would also be possible to stop if one scenario unacceptably fails to fulfil the clinical goals, which could mean that the plan will be unsuitable. In that case, the plan could be modified and evaluated again. As will be understood, the calculations of step S59 may be postponed so that the probabilities of all scenarios of fulfilling the clinical goals are calculated in step S61.

Preferably, to speed up the calculations, the dose contribution to the patient for each interpolation spot has been precalculated so that it can be obtained from a database or other type of memory instead of being calculated again for each new evaluation. In this way, the dose of a simulated treatment can be calculated as a sum of pre-existing values weighted by the interpolated weights, in step S55.

Fredriksson, Forsgren and Hårdemark: Maximizing the probability of satisfying the clinical goals in radiation therapy treatment planning under setup uncertainty, Medical Physics, Vol. 42, No. 7, July 2015, discloses a way of taking uncertainties into account to achieve robust optimization of a treatment plan. It does not, however discuss how to evaluate the robustness of an existing treatment plan.

If biologically corrected total doses are desired, the interpolation can be used to calculate a large number of single-fraction scenario doses, which can then be combined using arbitrary (non-linear) functions.

The evaluation of a plan is made to determine the probability of fulfilling the clinical goals to a certain percentage. Given the doses for simulated treatments, the list of clinical goals could be extended with a column displaying the probability of fulfilling the goal. For example, the goals could include 90% probability of target coverage and 90% probability of sparing an organ at risk. Moreover, one or more groups of goals could be selected and the probability of simultaneously fulfilling the goals, for example a group consisting of the two goals above, could be evaluated. As an example, the probability of simultaneously fulfilling both goals could be 81-90%.

The doses that have been calculated according to the above may be displayed in any suitable way, for example, as superimposed DVH curves, DVH bands or superimposed on the patient image. It is also possible to display voxel-wise statistics related to the dose, such as the worst dose to any given voxel over all of the scenarios, or the average value to each voxel with standard deviation.

Figure 6:
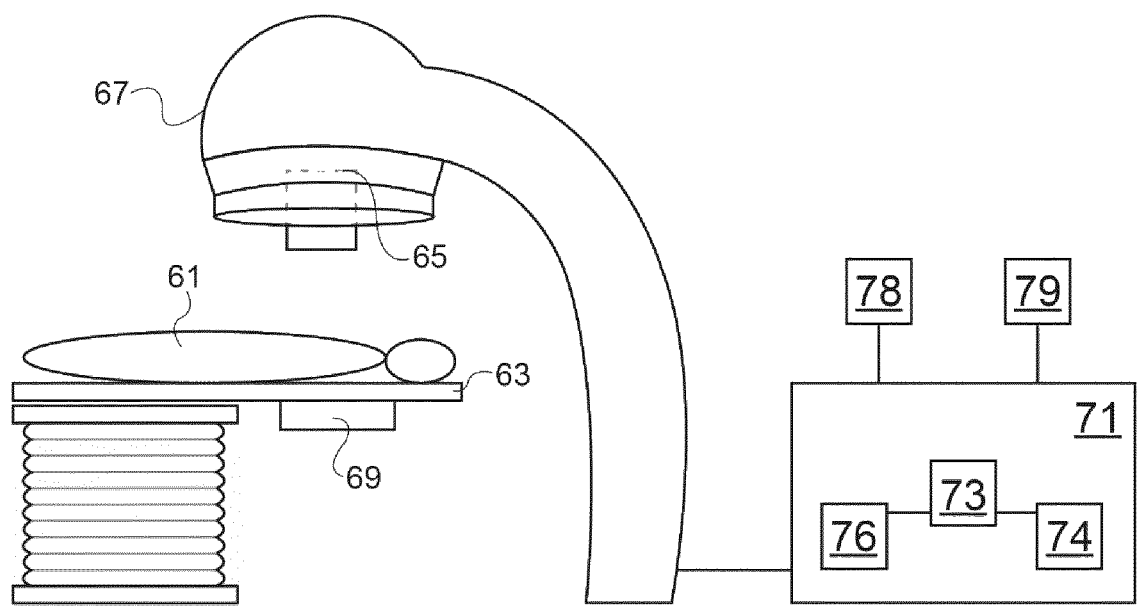
FIG. 6 is a schematic overview of a radiotherapy treatment system in which the method according to embodiments of the invention may be implemented.

FIG. 6 is an overview of a system for radiotherapy treatment imaging and/or planning. As will be understood, such systems may be designed in any suitable way and the design shown in FIG. 6 is only an example. A patient 61 is positioned on a treatment couch 63. The system comprises an imaging unit having a radiation source 65 mounted in a gantry 67 for emitting radiation towards the patient positioned on the couch 63. Typically, the couch 63 and the gantry 67 are movable in several dimensions relative to each other, to provide radiation to the patient as flexibly and correctly as possible. If the system is used for imaging, there is also a detector 69 positioned at a suitable place, typically on the opposite side of the couch 63 from the gantry 67. These parts are well known to the skilled person. The system also comprises a computer 71 which may be used for radiotherapy treatment planning and/or for controlling radiotherapy treatment. As will be understood, the computer 71 may be a separate unit not connected to the imaging unit.

The computer 71 comprises a processor 73, a data memory 74, and a program memory 76. Preferably, one or more user input means 78, 79 are also present, in the form of a keyboard, a mouse, a joystick, voice recognition means or any other available user input means. The user input means may also be arranged to receive data from an external memory unit.

The data memory 74 comprises clinical data and/or other information used to obtain a treatment plan, including a set of clinical goals to be used for planning. The data memory 74 also comprises one or more dose maps for one or more patients to be used in treatment planning according to embodiments of the invention. The program memory 76 holds a computer program, known per se, arranged for treatment plan optimization. The program memory 76 also holds a computer program arranged to make the computer perform the method steps discussed in connection with FIG. 3 and/or a computer program arranged to make the computer perform the method steps discussed in connection with FIG. 5.

As will be understood, the data memory 74 and the program memory 76 are shown and discussed only schematically. There may be several data memory units, each holding one or more different types of data, or one data memory holding all data in a suitably structured way, and the same holds for the program memories. One or more memories may also be stored on other computers. For example, the computer may only be arranged to perform one of the methods, there being another computer for performing the optimization.

The invention claimed is:

1. A computer-implemented method of evaluating the robustness of a radiotherapy treatment plan comprising a plurality of treatment fractions, comprising the steps of:
   a. obtaining a plan to be evaluated;
   b. defining a scenario comprising one or more errors for each fraction of the plurality of treatment fractions such that at least two fractions of the plurality of treatment fractions comprise different errors;
   c. performing, by a processing means, a computer-implemented simulation of the plan under the defined scenario to calculate a dose distribution resulting from the simulated plan under the scenario, wherein the contribution from each beam to a total dose distribution resulting from the scenario is approximated by a single beam dose calculation;
   d. repeating steps b. and c. for a number of different scenarios; and
   e. evaluating, by the processing means, the robustness of the plan by comparing the dose distribution as calculated via the computer-implemented simulation for each of the scenarios with a set of clinical goals, based on at least one of the following:
      i. the probability of fulfilling the set of clinical goals estimated as the clinical goal fulfilment over the scenarios;
      ii. a range of dose-volume histogram (DVH) values over the scenarios; and
      iii. dose statistics for dose distributions defined as voxel-wise aggregates over the scenario doses,
   wherein the calculated dose distribution is configured to be displayed such that the dose distribution of the simulated plan is superimposed on a patient image.

2. The method according to claim 1, wherein steps a-d are performed such that the evaluation of the plan is based on at least one of the following:
   one or more patient images;
   one or more artificial patient images; or
   one or more density errors.

3. The method according to claim 1, wherein the one or more errors for each fraction includes at least a systematic error that affects all fractions and/or at least a fraction-specific error.

4. The method according to claim 1, wherein a single fluence distribution for each beam direction and energy is used to calculate an approximation of the total dose distribution resulting from a scenario.

5. The method according to claim 4, wherein the single fluence distribution for each beam and energy is calculated as the sum of the fluence distributions for all fractions translated according to their corresponding setup errors projected onto a fluence plane of the beam.

6. The method according to claim 5, wherein the fluence distribution in each fraction is scaled according to a constituent of its corresponding setup error that is orthogonal to the fluence plane of the beam.

7. The method according to claim 1, for a spot scanning ion based treatment plan, wherein a single set of spot weights for each beam is used to calculate an approximation of the total dose distribution resulting from a scenario.

8. The method according to claim 7, wherein the single set of spot weights for each beam is calculated as the sum of the spot weights for all fractions, the spot weights for each fraction being calculated by translating the spot positions according to a corresponding setup error of the fractions projected onto the spot plane, changing the energy of the spots according to a range or density error of the fraction, and allocating the spot weights associated with the translated spot positions to the existing non-translated spot positions by interpolating spot weights between spots.

9. The method according to claim 8, wherein the spot weights in each fraction are scaled according to a constituent of its corresponding setup error that is orthogonal to the spot plane of the beam.

10. The method according to claim 8, wherein the step of interpolating spot weights between spots comprises the steps of determining auxiliary spots at a distance from the planning spots, said distance depending on at least one assumed shift in the relative position between the patient and the spot planes or the radiation source, and including the auxiliary spots in the interpolation.

11. The method according to claim 1, further comprising the step of obtaining a set of clinical goals, including at least one clinical goal for the plan to be evaluated, the set used to create the plan to be evaluated.

12. The method according to claim 11, further including step c2. determining whether the at least one clinical goal was fulfilled for the dose distribution calculated in step c, and wherein step d. involves repeating steps b., c., and c2 for different scenarios, and wherein step e. involves approximating the probability of satisfying the at least one clinical goal by the fraction of scenarios under the at least one clinical goal was fulfilled in step c2.

13. A non-transitory computer-readable medium comprising instructions which, when run in a computer, causes the computer to perform a method according to claim 1.

14. A treatment planning system comprising a processor, a data memory comprising data for obtaining a treatment plan, including a set of clinical goals to be used for planning, and the non-transitory computer-readable medium according to claim 13.

15. A computer-implemented method of evaluating the robustness of a radiotherapy treatment plan comprising a number of treatment fractions, comprising the steps of:
   a. obtaining a plan to be evaluated;
   b. defining a scenario comprising one or more errors for each fraction;
   c. calculating a dose distribution resulting from the plan under the scenario, wherein the contribution from each beam to the total dose distribution resulting from a scenario is approximated by a single beam dose calculation, wherein when the treatment plan is a spot scanning ion based treatment plan, a single set of spot weights for each beam is used to calculate an approximation of the total dose distribution resulting from a scenario, and the single set of spot weights for each beam is calculated as the sum of the spot weights for all fractions, the spot weights for each fraction being calculated by translating the spot positions according to the fraction's corresponding setup error projected onto a spot plane, changing the energy of the spots according to the range or density error of the fraction, and allocating the spot weights associated with the translated spot positions to the existing non-translated spot positions by interpolating spot weights between spots;

d. repeating steps b. and c. for a number of different scenarios; and e. evaluating the robustness of the plan by comparing the calculated dose distribution for each scenario with a set of clinical goals, based on at least one of the following:
   i. the probability of fulfilling the set of clinical goals estimated as the clinical goal fulfilment over the scenarios;
   ii. a range of dose-volume histogram (DVH) values over the scenarios; and
   iii. dose statistics for dose distributions defined as voxel-wise aggregates over the scenario doses.

16. The method according to claim 15, wherein the spot weights in each fraction are scaled according to a constituent of its corresponding setup error that is orthogonal to the spot plane of the beam.

17. The method according to claim 15, wherein the step of interpolating spot weights between spots comprises the steps of determining auxiliary spots at a distance from the planning spots, said distance depending on at least one assumed shift in the relative position between the patient and the spot plane or the radiation source, and including the auxiliary spots in the interpolation.

18. A computer-implemented method of evaluating the robustness of a radiotherapy treatment plan comprising a number of treatment fractions, comprising the steps of:

a. obtaining a plan to be evaluated and a set of clinical goals, including at least one clinical goal for the plan to be evaluated, preferably the set used to create the plan to be evaluated;

b. defining a scenario comprising one or more errors for each fraction;

c. calculating a dose distribution resulting from the plan under the scenario, wherein the contribution from each beam to the total dose distribution resulting from a scenario is approximated by a single beam dose calculation;

d. determining whether the at least one clinical goal was fulfilled for the calculated dose distribution;

e. repeating steps b., c., and d. for a number of different scenarios;

f. approximating a probability of satisfying the at least one clinical goal by the fraction of scenarios under the at least one clinical goal that was fulfilled in step d.; and g. evaluating the robustness of the plan by comparing the calculated dose distribution for each scenario with the set of clinical goals, based on at least one of the following:
   i. the probability of fulfilling the set of clinical goals estimated as the clinical goal fulfilment over the scenarios;
   ii. a range of dose-volume histogram (DVH) values over the scenarios; and
   iii. dose statistics for dose distributions defined as voxel-wise aggregates over the scenario doses.

* * * * *